United States Patent
Moore et al.

(10) Patent No.: US 11,382,763 B2
(45) Date of Patent: Jul. 12, 2022

(54) INTERBODY SPACER

(71) Applicant: K2M, Inc., Leesburg, VA (US)

(72) Inventors: Jennifer Moore, Leesburg, VA (US);
Megan Carnes, Leesburg, VA (US);
Todd Wallenstein, Ashburn, VA (US);
Clint Boyd, Leesburg, VA (US);
Jordan Floyd, Westlake, OH (US);
Stephen Truesdell, Reston, VA (US)

(73) Assignee: K2M, Inc., Leesburg, VA (US)

( * ) Notice: Subject to any disclaimer, the term of this patent is extended or adjusted under 35 U.S.C. 154(b) by 77 days.

(21) Appl. No.: 17/084,074

(22) Filed: Oct. 29, 2020

(65) Prior Publication Data

US 2021/0038407 A1 Feb. 11, 2021

Related U.S. Application Data

(63) Continuation of application No. 16/039,701, filed on Jul. 19, 2018, now Pat. No. 10,849,764, which is a
(Continued)

(51) Int. Cl.
*A61F 2/44* (2006.01)
*A61F 2/30* (2006.01)
*A61F 2/46* (2006.01)

(52) U.S. Cl.
CPC ........ *A61F 2/4455* (2013.01); *A61F 2/30771* (2013.01); *A61F 2/446* (2013.01);
(Continued)

(58) Field of Classification Search
CPC .......... A61F 2/44; A61F 2/4455; A61F 2/446; A61F 2/4465; A61F 2/447;
(Continued)

(56) References Cited

U.S. PATENT DOCUMENTS 2,375,116 A 5/1945 Larkin
5,192,327 A 3/1993 Brantigan
(Continued)

FOREIGN PATENT DOCUMENTS

CN 103445883 A 12/2013
DE 102008024281 A1 12/2009
(Continued)

OTHER PUBLICATIONS

Williams et al., CT Evaluation of Lumbar Interbody Fusion: Current Concepts, AJNR Am J Neuroradiol 26:2057-2066, Sep. 2005.
(Continued)

*Primary Examiner* — Eric S Gibson
(74) *Attorney, Agent, or Firm* — Lerner, David, Littenberg, Krumholz & Mentlik, LLP (57) ABSTRACT

An interbody spacer is provided including a body portion defining a longitudinal axis. The body portion includes a distal end portion, a proximal end portion, opposed side surfaces that extend between the distal and proximal end portions, and top and bottom surfaces configured and adapted to engage vertebral bodies. The interbody spacer includes first orifices defined through the top surface. The first orifices include orifices having first and second cross-sectional configurations and the first orifices are arranged in rows extending along the longitudinal axis.

14 Claims, 5 Drawing Sheets

Related U.S. Application Data continuation of application No. 15/007,879, filed on Jan. 27, 2016, now Pat. No. 10,028,841.

(60) Provisional application No. 62/240,662, filed on Oct. 13, 2015, provisional application No. 62/196,371, filed on Jul. 24, 2015, provisional application No. 62/108,197, filed on Jan. 27, 2015.

(52) U.S. Cl.
CPC ............ *A61F 2/447* (2013.01); *A61F 2/4465* (2013.01); *A61F 2002/3079* (2013.01); *A61F 2002/3082* (2013.01); *A61F 2002/30772* (2013.01); *A61F 2002/30777* (2013.01); *A61F 2002/30784* (2013.01); *A61F 2002/30904* (2013.01); *A61F 2002/4692* (2013.01)

(58) Field of Classification Search
CPC .......... A61F 2/30771; A61F 2002/4692; A61F 2002/30772; A61F 2002/30777; A61F 2002/30784; A61F 2002/3079; A61F 2002/30792; A61F 2002/3082; A61F 2002/30904

See application file for complete search history.

(56) References Cited

U.S. PATENT DOCUMENTS

| | | | |
|---|---|---|---|
| 5,534,031 A | 7/1996 | Matsuzaki et al. | |
| 5,595,703 A | 1/1997 | Swaelens et al. | |
| 5,609,635 A | 3/1997 | Michelson | |
| 5,634,926 A | 6/1997 | Jobe | |
| 5,702,449 A | 12/1997 | McKay | |
| 5,733,286 A | 3/1998 | Errico et al. | |
| 5,768,134 A | 6/1998 | Swaelens et al. | |
| 5,786,134 A | 7/1998 | Nair et al. | |
| 5,943,235 A | 8/1999 | Earl et al. | |
| 5,968,098 A | 10/1999 | Winslow | |
| 6,010,502 A | 1/2000 | Bagby | |
| 6,039,762 A | 3/2000 | McKay | |
| 6,129,730 A | 10/2000 | Bono et al. | |
| 6,143,033 A | 11/2000 | Paul et al. | |
| 6,245,108 B1 | 6/2001 | Biscup | |
| 6,342,055 B1 | 1/2002 | Eisermann et al. | |
| 6,391,058 B1 | 5/2002 | Kuslich et al. | |
| 6,409,765 B1 | 6/2002 | Bianchi | |
| 6,432,107 B1 | 8/2002 | Ferree | |
| 6,454,811 B1 | 9/2002 | Sherwood et al. | |
| 6,520,996 B1 | 2/2003 | Manasas et al. | |
| 6,530,955 B2 | 3/2003 | Boyle et al. | |
| 6,530,956 B1 * | 3/2003 | Mansmann | A61L 27/3852 |
| | | | 623/18.11 |
| 6,716,247 B2 | 4/2004 | Michelson | |
| 6,730,127 B2 | 5/2004 | Michelson | |
| 6,758,849 B1 | 7/2004 | Michelson | |
| 6,855,167 B2 | 2/2005 | Shimp et al. | |
| 7,018,416 B2 | 3/2006 | Hanson et al. | |
| 7,238,206 B2 * | 7/2007 | Lange | A61F 2/4465 |
| | | | 623/17.11 |
| 7,509,183 B2 | 3/2009 | Lin et al. | |
| 7,645,301 B2 | 1/2010 | Hudgins et al. | |
| 7,665,979 B2 | 2/2010 | Heugel | |
| D623,749 S | 9/2010 | Horton | |
| 7,806,911 B2 | 10/2010 | Peckham | |
| 7,909,872 B2 | 3/2011 | Zipnick et al. | |
| D664,252 S | 7/2012 | Weiland et al. | |
| 8,275,594 B2 | 9/2012 | Lin et al. | |
| 8,287,541 B2 | 10/2012 | Nelson et al. | |
| 8,403,986 B2 | 3/2013 | Michelson | |
| 8,439,977 B2 | 5/2013 | Kostuik et al. | |
| 8,449,463 B2 | 5/2013 | Nunley et al. | |
| 8,449,585 B2 | 5/2013 | Wallenstein et al. | |
| 8,585,761 B2 | 11/2013 | Theofilos | |
| 8,590,157 B2 | 11/2013 | Kruth et al. | |
| 8,597,359 B2 | 12/2013 | Butler | |
| 8,669,043 B2 | 3/2014 | Mills et al. | |
| 8,673,011 B2 | 3/2014 | Theofilos et al. | |
| 8,697,231 B2 | 4/2014 | Longepied et al. | |
| 8,784,721 B2 | 7/2014 | Philippi et al. | |
| 8,801,791 B2 * | 8/2014 | Soo | A61F 2/30771 |
| | | | 623/17.11 |
| 8,814,919 B2 | 8/2014 | Barrus et al. | |
| 8,843,229 B2 | 9/2014 | Vanasse et al. | |
| 8,870,957 B2 * | 10/2014 | Vraney | A61F 2/447 |
| | | | 623/17.11 |
| 8,903,533 B2 | 12/2014 | Eggers et al. | |
| 8,932,356 B2 * | 1/2015 | Kraus | A61F 2/4465 |
| | | | 623/17.16 |
| 8,967,990 B2 | 3/2015 | Weidinger et al. | |
| 8,999,711 B2 | 4/2015 | Harlow et al. | |
| 9,011,982 B2 | 4/2015 | Muller et al. | |
| 9,247,970 B2 | 2/2016 | Teisen | |
| 9,283,078 B2 | 3/2016 | Roels et al. | |
| D786,434 S | 5/2017 | Trautwein | |
| 9,700,431 B2 | 7/2017 | Nebosky et al. | |
| 9,931,148 B2 | 4/2018 | Grady, Jr. et al. | |
| 9,987,051 B2 | 6/2018 | Nunley et al. | |
| 10,028,841 B2 * | 7/2018 | Moore | A61F 2/446 |
| 10,849,764 B2 * | 12/2020 | Moore | A61F 2/447 |
| 11,058,550 B2 * | 7/2021 | LaNeve | A61F 2/30771 |
| 2001/0047207 A1 | 11/2001 | Michelson | |
| 2001/0047208 A1 | 11/2001 | Michelson | |
| 2002/0120334 A1 | 8/2002 | Crozet | |
| 2002/0128714 A1 | 9/2002 | Manasas et al. | |
| 2003/0040798 A1 | 2/2003 | Michelson | |
| 2003/0135276 A1 * | 7/2003 | Eckman | A61F 2/4611 |
| | | | 623/17.11 |
| 2004/0024400 A1 | 2/2004 | Michelson | |
| 2004/0034352 A1 | 2/2004 | Needham et al. | |
| 2004/0243237 A1 | 12/2004 | Unwin et al. | |
| 2004/0249471 A1 | 12/2004 | Bindseil et al. | |
| 2005/0010226 A1 | 1/2005 | Grady et al. | |
| 2005/0021151 A1 | 1/2005 | Landis | |
| 2005/0055099 A1 | 3/2005 | Ku | |
| 2005/0112397 A1 | 5/2005 | Rolfe et al. | |
| 2005/0137597 A1 | 6/2005 | Butler et al. | |
| 2005/0149192 A1 | 7/2005 | Zucherman et al. | |
| 2005/0165400 A1 | 7/2005 | Fernandez | |
| 2005/0177238 A1 | 8/2005 | Khandkar et al. | |
| 2005/0246021 A1 | 11/2005 | Ringeisen et al. | |
| 2006/0235403 A1 | 10/2006 | Blain | |
| 2006/0247772 A1 | 11/2006 | McKay | |
| 2006/0264946 A1 | 11/2006 | Young | |
| 2007/0233272 A1 | 10/2007 | Boyce et al. | |
| 2007/0260324 A1 | 11/2007 | Joshi et al. | |
| 2007/0270812 A1 | 11/2007 | Peckham | |
| 2007/0270965 A1 | 11/2007 | Ferguson | |
| 2008/0097444 A1 | 4/2008 | Erickson et al. | |
| 2008/0154379 A1 | 6/2008 | Steiner | |
| 2008/0312743 A1 | 12/2008 | Vila et al. | |
| 2009/0018584 A1 | 1/2009 | Henderson, Sr. et al. | |
| 2009/0048673 A1 | 2/2009 | Bhatnagar et al. | |
| 2009/0054930 A1 | 2/2009 | Aflatoon | |
| 2009/0093881 A1 | 4/2009 | Bandyopadhyay et al. | |
| 2009/0270986 A1 | 10/2009 | Christensen | |
| 2009/0291308 A1 | 11/2009 | Pfister et al. | |
| 2009/0295042 A1 | 12/2009 | Pfister et al. | |
| 2010/0004747 A1 | 1/2010 | Lin | |
| 2010/0100131 A1 | 4/2010 | Wallenstein | |
| 2010/0137990 A1 | 6/2010 | Apatsidis et al. | |
| 2010/0228369 A1 | 9/2010 | Eggers et al. | |
| 2010/0234966 A1 | 9/2010 | Lo | |
| 2010/0268339 A1 * | 10/2010 | Malinin | A61F 2/447 |
| | | | 623/17.11 |
| 2011/0144752 A1 | 6/2011 | Defelice et al. | |
| 2011/0165340 A1 | 7/2011 | Baumann | |
| 2011/0168091 A1 | 7/2011 | Baumann et al. | |
| 2011/0190888 A1 | 8/2011 | Bertele et al. | |
| 2011/0190904 A1 | 8/2011 | Lechmann et al. | |
| 2011/0301709 A1 * | 12/2011 | Kraus | A61F 2/4465 |
| | | | 623/17.11 |
| 2012/0046750 A1 | 2/2012 | Obrigkeit et al. | |

(56) References Cited

U.S. PATENT DOCUMENTS

| | | |
|---|---|---|
| 2012/0143334 A1 | 6/2012 | Boyce et al. |
| 2012/0158062 A1 | 6/2012 | Nunley et al. |
| 2012/0179261 A1 | 7/2012 | Soo |
| 2012/0191188 A1 | 7/2012 | Huang |
| 2012/0191189 A1 | 7/2012 | Huang |
| 2012/0203229 A1 | 8/2012 | Appenzeller et al. |
| 2012/0303128 A1 | 11/2012 | Ullrich, Jr. et al. |
| 2012/0310364 A1 | 12/2012 | Li et al. |
| 2012/0316650 A1 | 12/2012 | Ullrich, Jr. et al. |
| 2013/0046345 A1 | 2/2013 | Jones et al. |
| 2013/0110243 A1 | 5/2013 | Patterson et al. |
| 2013/0116793 A1* | 5/2013 | Kloss ............... A61F 2/442 623/17.16 |
| 2013/0150893 A1 | 6/2013 | Kirschman |
| 2013/0171019 A1 | 7/2013 | Gessler et al. |
| 2013/0184765 A1 | 7/2013 | Beyar et al. |
| 2013/0273131 A1 | 10/2013 | Frangov et al. |
| 2014/0088716 A1 | 3/2014 | Zubok et al. |
| 2014/0107785 A1* | 4/2014 | Geisler ............... A61F 2/442 623/17.16 |
| 2014/0107786 A1* | 4/2014 | Geisler ............ A61F 2/30965 623/17.16 |
| 2014/0172111 A1 | 6/2014 | Lang et al. |
| 2014/0277491 A1 | 9/2014 | Fang et al. |
| 2015/0018956 A1* | 1/2015 | Steinmann ......... A61F 2/4465 419/53 |
| 2015/0045924 A1 | 2/2015 | Cluckers et al. |
| 2015/0134063 A1* | 5/2015 | Steinmann ......... A61F 2/4465 623/17.16 |
| 2015/0142158 A1 | 5/2015 | Szwedka |
| 2015/0367575 A1 | 12/2015 | Roels et al. |
| 2016/0022431 A1* | 1/2016 | Wickham ............ A61F 2/447 623/17.16 |
| 2016/0038301 A1* | 2/2016 | Wickham ........... A61F 2/4455 623/17.16 |
| 2016/0058575 A1 | 3/2016 | Sutterlin, III et al. |
| 2016/0199193 A1* | 7/2016 | Willis ................. B22F 7/002 623/17.16 |
| 2016/0213485 A1* | 7/2016 | Schaufler ............. A61F 2/447 |
| 2016/0213486 A1 | 7/2016 | Nunley et al. |
| 2016/0213487 A1 | 7/2016 | Wilson et al. |
| 2016/0213488 A1* | 7/2016 | Moore ............... A61F 2/4465 |
| 2018/0325692 A1* | 11/2018 | Moore ............. A61F 2/30771 |
| 2019/0298542 A1* | 10/2019 | Kloss ................. A61F 2/3094 |
| 2019/0328546 A1 | 10/2019 | Palagi et al. |
| 2021/0038407 A1* | 2/2021 | Moore ............... A61F 2/4465 |

FOREIGN PATENT DOCUMENTS

| | | |
|---|---|---|
| DE | 102008024288 A1 | 12/2009 |
| EP | 0425542 B1 | 3/1995 |
| EP | 1464307 A1 | 10/2004 |
| EP | 1905391 B1 | 1/2010 |
| EP | 2145913 A1 | 1/2010 |
| EP | 2457538 A1 | 5/2012 |
| EP | 1772108 B1 | 11/2015 |
| WO | 9000037 A1 | 1/1990 |
| WO | 9405235 A1 | 3/1994 |
| WO | 9419174 A1 | 9/1994 |
| WO | 9510248 A1 | 4/1995 |
| WO | 9532673 A1 | 12/1995 |
| WO | 9608360 A1 | 3/1996 |
| WO | 9628117 A1 | 9/1996 |
| WO | 9640015 A1 | 12/1996 |
| WO | 9640019 A1 | 12/1996 |
| WO | 9734546 A1 | 9/1997 |
| WO | 0025707 A1 | 5/2000 |
| WO | 0040177 A1 | 7/2000 |
| WO | 0066045 A1 | 11/2000 |
| WO | 0202151 A2 | 1/2002 |
| WO | 0230337 A2 | 4/2002 |
| WO | 02080820 A1 | 10/2002 |
| WO | 2006101837 A2 | 9/2006 |
| WO | 2009068021 A1 | 6/2009 |
| WO | 2011030017 A1 | 3/2011 |
| WO | 201317647 A1 | 2/2013 |
| WO | 2013155500 A1 | 10/2013 |
| WO | 2013156545 A1 | 10/2013 |
| WO | 201496294 A1 | 6/2014 |

OTHER PUBLICATIONS

Akamaru et al., Healing of Autologous Bone in a Titanium Mesh Cage Used in Anterior Column Reconstruction After Total Spondylectomy; Spine vol. 27, No. 13, pp. E329-E333, Jan. 2002.
McAfee, Interbody Fusion Cages in Reconstructive Operations on the Spine, The Journal of Bone and Joint Surgery Incorporated, vol. 81A, No. 6, Jun. 1999, pp. 859-880.
Zdeblick, et al., L T-Cage Lumbar Tapered Fusion Device Surgical Technique, Medtronic, pp. 1-25, 2000.
Kuslich, Lumbar Interbody Cage Fusion for Back Pain: An Update on the Bak (Bagby and Kuslich) System, Spine: State of the Art Reviews; vol. 13, No. 2, May 1999, pp. 295-311.
Cheung et al., Spinal Instrumentation Overview in Lumbar Degenerative Disorders: Cages, Lumbar Spine: Official Publication of the International Society for the Study of Lumbar Spine (3), pp. 286-291, 2004.
Sasso, Screws, Cages or Both?, <http://www.spineuniverse.com/professional/technology/surgical/thoracic/>, pp. 1-11, Sep. 2012.
Costa et al., Stand-alone cage for posterior lumbar interbody fusion in the treatment of high-degree degenerative disc disease: design of a new device for an "old" technique. A prospective study on a series of 116 patients, Eur Spine J, May 2011: 20 (Suppl 1), pp. 46-56.
Chong et al., The design evolution of interbody cages in anterior cervical discectomy and fusion: a systematic review; BMC Musculoskeletal Disorders Apr. 2015 16:99, pp. 1-20.
Synthes Contact Fusion Cage, Technique Guide, 2007, pp. 1-16.
Stryker, Ttritanium basic science summary, technical monograph, pp. 1-2, 2016.
EBI Spine Flyer, North American Spine Society 20th Annual Meeting, Sep. 27-Oct. 1, 2005.
Fukuda A, Takemoto M, Tanaka K, Fujibayashi S, Pattanayak DK, Matsushita T, Sasaki K, Nishida N, Kokubo T, Nakamura T. Bone ingrowth into pores of lotus stem-type bioactive titanium implants fabricated using rapid prototyping technique. Bioceramics Development and Applications. Jan. 2011 1;1, 3 pages.
Cunningham et al, Design of Interbody Fusion Cages: Historical Considerations and Current Perspectives in Cage Technology; Surgical Techniques, Spinal Implants, pp. 421-465, 2006.
Lin et al., Interbody Fusion Gage Design Using Integrated Global Layout and Local Microstructure Topology Optimization; Spine, vol. 29, No. 16, pp. 1747-1754,2004.
Sofamor Danek Interfix Thread Fusion Device, pp. 32-45, 1999.
Lin, et al. Structural and mechanical evaluations of a topology optimized titanium interbody fusion cage fabricated by selective laser melting process, Journal of Biomedical Materials Research Part A DOI 10.1 002/jbm.a, pp. 272-279, Apr. 2007.
Kim et al. Spinal Instrumentation Surgical Techniques, Thieme Medical publishers, 2004, pp. 232-245, 518-524, p. 32-537, 736-743, 795-800.
Bridwell et al . . . , Specialty Update, What's New in Spine Surgery, The Journal of Bone and Joint Surgery, Incorporated, pp. 1022-1030, Core 1st page of article, Jun. 2015.
Extended European Search Report for EP 16 15 2952 dated Jul. 1, 2016.
Extended European Search Report including the Written Opinion for Application No. EP 16856190.0 dated May 28, 2019.
Australian Examination Report for Application No. 2016200443 dated Sep. 11, 2019, 4 pages.
International Search Report and Written Opinion for PCT/US16/56834 dated Jan. 12, 2017.
EBI Spine, Promotional flyer, 1 page 2005.

* cited by examiner

INTERBODY SPACER

CROSS-REFERENCE TO RELATED APPLICATIONS

This application is a continuation application of U.S. patent application Ser. No. 16/039,701, filed Jul. 19, 2018, which is a continuation application of U.S. patent application Ser. No. 15/007,879, filed on Jan. 27, 2016, which claims priority to, and the benefit of, U.S. Provisional Patent Application Ser. No. 62/108,197, filed on Jan. 27, 2015, U.S. Provisional Patent Application Ser. No. 62/196,371, filed on Jul. 24, 2015, and U.S. Provisional Patent Application Ser. No. 62/240,662, filed Oct. 13, 2015. The entire contents of each of these prior applications are hereby incorporated by reference herein.

BACKGROUND

Technical Field

The present disclosure relates to an apparatus for treating spinal conditions, and more particularly, to an interbody spacer and a method of use therefor.

Background of Related Art

The human spinal column is a highly complex structure. It includes twenty-four discrete bones, known as vertebrae, coupled sequentially to one another to house and protect critical elements of the nervous system. The vertebrae interlock with one another to form a spinal column. Each vertebra has a cylindrical bony body (vertebral body), two pedicles extending from the vertebral body, a lamina extending from the pedicles, two wing-like projections extending from the pedicles, a spinous process extending from the lamina, a pars interarticularis, two superior facets extending from the pedicles, and two inferior facets extending from the lamina.

The vertebrae are separated and cushioned by thin pads of tough, resilient fiber known as inter-vertebral discs. Intervertebral discs provide flexibility to the spine and act as shock absorbers during activity. A small opening (foramen) located between each vertebra allows passage of nerves. When the vertebrae are properly aligned, the nerves pass through without a problem. However, when the vertebrae are misaligned or a constriction is formed in the spinal canal, the nerves get compressed and may cause back pain, leg pain, or other neurological disorders.

For many reasons, such as aging and trauma, the intervertebral discs can begin to deteriorate and weaken, potentially resulting in chronic pain, degenerative disc disease, or even tearing of the disc. Ultimately, the disc may deteriorate or weaken to the point of tearing and herniation, in which the inner portions of the disc protrude through the tear. A herniated disc may press against, or pinch, the spinal nerves, thereby causing radiating pain, numbness, tingling, and/or diminished strength or range of motion.

Many treatments are available to remedy these conditions, including surgical procedures in which one or more damaged intervertebral discs are removed and replaced with a prosthetic. After a partial or complete discectomy, the normally occupied space between adjacent vertebral bodies is subject to collapse and/or misalignment due to the absence of all or part of the intervertebral disc. In such situations, the physician may insert one or more prosthetic spacers between the affected vertebrae to maintain normal disc spacing and/or the normal amount of lordosis in the affected region.

Typically, a prosthetic implant is inserted between the adjacent vertebrae and may include pathways that permit bone growth between the adjacent vertebrae until they are fused together. However, there exists a possibility that conventional prosthetic implants may be dislodged and moved from their desired implantation location due to movement by the patient before sufficient bone growth has occurred.

Bone growth is a key factor in ensuring adequate retention of the implant to the vertebra. Specifically, bone ingrowth within and around the prosthetic implant promotes fusion between the adjacent vertebra, thereby strengthening the joint therebetween. However, conventional implants do not allow optimal space for bone ingrowth. In these instances, as the prosthetic implants do not mimic bone density of the adjacent vertebra, the body may reject the implant, and non-union (i.e., no fusion) may occur.

Conventional prosthetic implants are typically constructed in a manner that inhibits bone ingrowth, particularly those that include no spaces or avenues for such bone growth to occur within and around the prosthetic implant. The lack of fusion may allow the implant to become dislodged or moved from its desired location. Additionally, in the instances where the prosthetic implant includes a lumen for the packing of ingrowth material, the material is often able to dislodge from the lumen, and in some instances, from the implant, thereby reducing the chances that adequate bone ingrowth occurs.

Therefore, a need exists for a prosthetic implant that can mimic the density of bone or adequately retain ingrowth material therein to allow for optimal bone ingrowth and provide a solid fusion of the vertebral segments.

SUMMARY

In accordance with an embodiment of the present disclosure, there is provided an interbody spacer including a body portion defining a longitudinal axis. The body portion includes a distal end portion, a proximal end portion, opposed side surfaces that extend between the distal and proximal end portions, and top and bottom surfaces configured and adapted to engage vertebral bodies. The interbody spacer includes first orifices defined through the top surface. The first orifices include orifices having first and second cross-sectional configurations and are arranged in rows extending along the longitudinal axis.

In embodiments, the second cross-sectional configuration may be larger than the first cross-sectional configuration. The first orifices may be arranged in each row of the longitudinal rows in an alternating pattern of orifices having first and second cross-sectional configurations.

In embodiments, the first orifices may include orifices with a third cross-sectional configuration, wherein the third cross-sectional configuration is larger than the second cross-sectional configuration. The first orifices may be arranged in each row of the longitudinal rows in a pattern, such that the cross-sectional configuration of each orifice of the first orifices increases from the first cross-sectional configuration to the third cross-sectional configuration. Alternatively, the first orifices may be arranged in a random pattern.

In embodiments, each orifice of the first orifices may include a cross-sectional configuration selected from the group consisting of arcuate, more than four sides, quadrilateral, triangle, and sinusoidal.

In embodiments, each orifice of the first orifices may include a cross-sectional configuration selected from the group consisting of oval, kidney, elliptical, circular, teardrop, semicircle, and ovoid.

In embodiments, each orifice of the first orifices may include a cross-sectional configuration selected form the group consisting of squircle, square, rhombus, trapezoid, and rectangle.

In embodiments, each orifice of the first orifices may include a cross-sectional configuration selected from the group consisting of hexagon, octagon, heptagon, and pentagon.

In embodiments, each orifice of the first orifices may include a cross-sectional configuration selected from the group consisting of isosceles, equilateral, scalene, arrowhead with arcuate base, and right.

In embodiments, each orifice of the first orifices may include a cross-sectional configuration selected from the group consisting of greek cross and clover.

In embodiments, second orifices may be defined through the bottom surface. One of the first orifices may include a cross-sectional configuration different than that of one of the second orifices. One of the first orifices may be offset from one of the second orifices.

In embodiments, a respective orifice of the first and second orifices may be in open communication, thereby defining a respective channel through the body portion. Each channel includes a cross-sectional configuration that varies in a direction from the top surface to the bottom surface.

In embodiments, each channel may include a sinusoidal cross-sectional configuration. Alternatively, each channel may include a cross-sectional configuration including spherical, cylindrical, frusto conical, ellipsoidal, hyperboloid, or any combination thereof. Alternatively, each channel may include a cross-sectional configuration including helical grooves disposed on an inner wall surface thereof.

In embodiments, a respective orifice of the first orifices may be in open communication with an orifice defined through one of the opposed side surfaces, thereby defining a respective channel through the body portion.

BRIEF DESCRIPTION OF THE DRAWINGS

Various embodiments of the present disclosure are described hereinbelow with reference to the drawings, wherein.

DETAILED DESCRIPTION OF EMBODIMENTS

Embodiments of the present disclosure are now described in detail with reference to the drawings in which like reference numerals designate identical or corresponding elements in each of the several views. As commonly known, the term "clinician" refers to a doctor, a nurse, or any other care provider and may include support personnel. Additionally, the term "proximal" refers to the portion of the device or component thereof that is closer to the clinician and the term "distal" refers to the portion of the device or component thereof that is farther from the clinician. In addition, the term "cephalad" is known to indicate a direction toward a patient's head, whereas the term "caudal" indicates a direction toward the patient's feet. Further still, for the purposes of this application, the term "lateral" indicates a direction toward a side of the body of the patient, i.e., away from the middle of the body of the patient. The term "posterior" indicates a direction toward the patient's back, and the term "anterior" indicates a direction toward the patient's front. Additionally, in the drawings and in the description that follows, terms such as front, rear, upper, lower, top, bottom, and similar directional terms are used simply for convenience of description and are not intended to limit the disclosure. In the following description, well-known functions or constructions are not described in detail to avoid obscuring the present disclosure in unnecessary detail.

Figure 1:
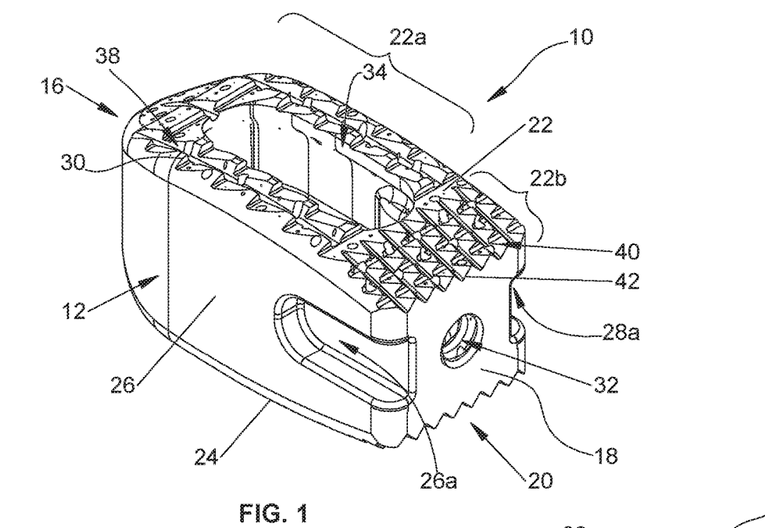
FIG. 1 is a rear, perspective view of an interbody spacer provided in accordance with the present disclosure.
Figure 2:
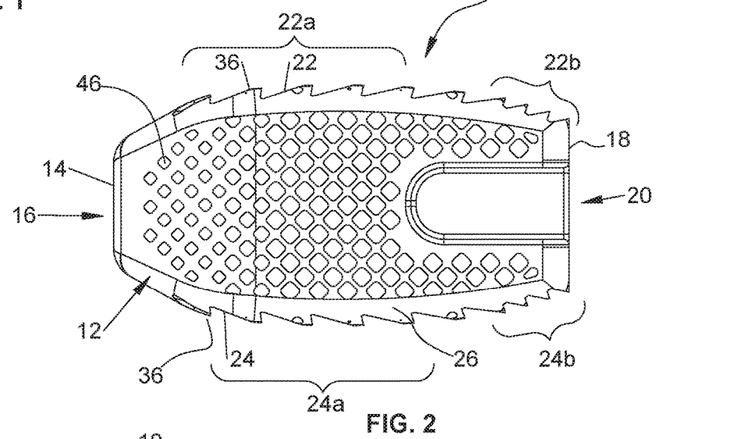
FIG. 2, is a side view of the interbody spacer of FIG. 1.
Figure 3:
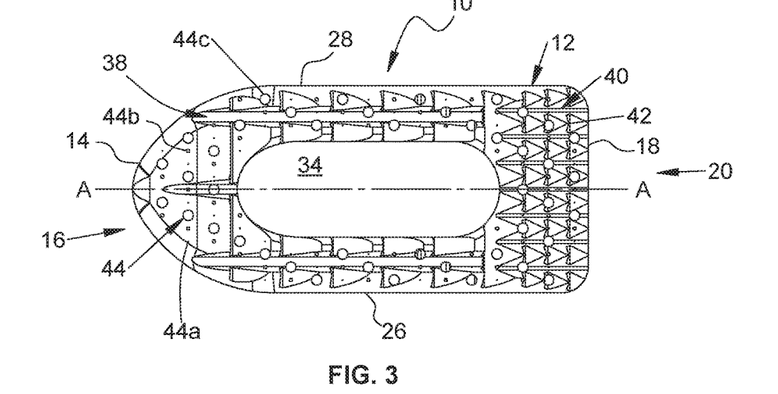
FIG. 3 is a top view of the interbody spacer of FIG. 1.

Referring now to the drawings, FIGS. 1-3 illustrate an interbody spacer provided in accordance with the present disclosure and generally identified by reference numeral 10. Interbody spacer 10 includes a body portion 12 having a substantially contoured first end surface 14 (FIG. 2) at a distal or leading end 16 and a second end surface 18 opposite thereto at a proximal or trailing end 20, having a substantially planar configuration. Axis A-A (FIG. 3) is defined through a midpoint of first and second end surfaces 14, 18, respectively. Body portion 12 extends between first and second end surfaces 14, 18 to define respective top and bottom surfaces 22 and 24 (FIG. 2), respectively, as well as opposed side surfaces 26, 28 (FIG. 3). As best illustrated in FIG. 2, top and bottom surfaces 22, 24 include a generally convex or arcuate profile, each extending in a cephalad and caudal direction (or vice-versa), respectively. Although shown and described as the top surface 22 being oriented in a cephalad direction and the bottom surface 24 being oriented in a caudal direction, the interbody spacer 10 may be positioned such that the top surface 22 is in a caudal orientation and the bottom surface 24 is in a cephalad orientation. As can be appreciated, top and bottom surfaces 22 and 24 may include a concave profile, a planar profile, or any combination thereof. In embodiments, top surface 22 may include a different profile than that of bottom surface 24. Additionally, it is contemplated that top and bottom surfaces 22, 24 may approximate in a direction along axis A-A (or vice-versa), or may approximate in a direction from side surface 26 towards side surface 28 (or vice-versa), or any combination thereof.

As best illustrated in FIG. 3, opposed side surfaces 26, 28 are substantially planar, although other configurations are also contemplated such as convex, concave, or the like. Opposed side surfaces 26, 28 approximate towards each other at distal end 16 along longitudinal axis A-A in order to facilitate insertion within the intervertebral space and enhance the atraumatic character of body portion 12. In this manner, the intersection of top and bottom surfaces 22, 24 with each of first and second end surfaces 14, 18 and opposed side surfaces 26, 28 may include a fillet or rounded configuration 30 to inhibit sharp edges from causing trauma to the surrounding tissue and/or vertebral bodies.

Referring again to FIG. 1, second end surface 18 includes an aperture 32 defined therethrough and extending along longitudinal axis A-A. Aperture 32 is configured for selective engagement with a suitable insertion tool (not shown), such as that described in U.S. Patent Application No. 2012/0158062, filed Oct. 11, 2011, the entire contents of which are hereby incorporated by reference herein. In embodiments, aperture 32 may be threaded or otherwise include various features capable of selectively retaining a suitable insertion tool (not shown) therein, such as a keyhole configuration, quarter-turn configuration, or the like.

Each of opposed side surfaces 26, 28 includes a corresponding depression or recess 26a, 28a defined therein adjacent second end surface 18. Recesses 26a, 28a extend along longitudinal axis A-A and are symmetrically disposed on each of opposed side surfaces 26, 28 to define a substantially I-shaped configuration to second end surface 18 at proximal end 20. In cooperation with aperture 32, the recesses 26a, 28a are further configured to enable engagement with stabilizing jaws of a suitable insertion instrument (not shown) to facilitate the insertion of interbody spacer 10. As can be appreciated, interbody spacer 10 may not include recesses 26a, 28a, and rather, include planar side surfaces 26, 28 that extend between first and second end surfaces 14, 18.

Body portion 12 includes a through-bore or cavity 34 defined through top and bottom surfaces 22, 24, respectively. Although shown as having a generally oval configuration, it is contemplated that through-bore 34 may include any suitable shape such as square, rectangular, circular, or the like, or may include a configuration similar to that of the outer perimeter of body portion 12. It is contemplated that through-bore 34 may receive allograft material, autograft material, calcium phosphate/bone marrow aspirate (BMA), autogenous material, synthetic materials comprised of a biocompatible osteoconductive, osteoinductive, or osteogeneic material such as VITOSS® Synthetic Cancellous Bone Void Filler material, or any other suitable biological material known in the art. Through-bore 34 includes a cross-sectional area or surface area that is greater than any orifice of the plurality of orifices or enlarged orifices detailed hereinbelow. In embodiments, through-bore 34 includes a surface area that is equal to or greater than 25% of the surface area of top surface 22 or bottom surface 24.

Top and bottom surfaces 22, 24 of body portion 12 are configured to engage respective endplates of adjacent vertebral bodies. In this manner, each of top and bottom surfaces 22, 24 includes at least first and second surface regions 22a, 22b and 24a, 24b, respectively, which have distinct surface characteristics. As best illustrated in FIG. 2, first surface regions 22a, 24a are disposed distal to second surface regions 22b, 24b and include a surface characteristic that is different than that of second surfaces 22b, 24b. In embodiments, first surface regions 22a, 24a may include a same or similar surface characteristic to that of second surface regions 22b, 24b, or each of first and second surface regions 22a, 24a and 22b, 24b may include the same or different surface characteristics, or any combination thereof.

First surface regions 22a, 24a each have a plurality of protrusions (i.e., teeth) or ridges 36 disposed thereof to aid in securing interbody spacer 10 to each respective adjacent vertebral body and stability against fore and aft, oblique or side to side movement of interbody spacer 10 within the intervertebral space. Specifically, protrusions 36 frictionally engage endplates of adjacent vertebral bodies and inhibit movement of the interbody spacer 10 with respect to the adjacent vertebral bodies. In embodiments, a plurality of longitudinal grooves 38 (FIGS. 1 and 3) may be defined within protrusions 36, each of which extends along longitudinal axis A-A. Each of second surface regions 22b, 24b includes substantially pyramidal protrusions 40, where each pyramidal protrusion 40 includes a plurality of protrusions or ridges disposed thereon to similarly aid in securing interbody spacer 10 to each respective adjacent vertebral body. In particular, each pyramidal protrusion 40 includes opposed first and second faces that face, respectively, distally and proximally. Further, each pyramidal protrusion 40 has third and fourth faces that face, respectively, medially and laterally. For a detailed description of an interbody spacer having exemplary surface characteristics, reference can be made to U.S. Pat. No. 8,801,791 to Soo et al., filed Sep. 27, 2007, the entire contents of which are hereby incorporated by reference herein.

Interbody spacer 10 is constructed of a biocompatible material, such as commercially pure titanium or titanium alloy and includes a porosity capable of promoting bone ingrowth and fusion with interbody spacer 10. In this manner, top and bottom surfaces 22, 24 and opposed side surfaces 26, 28 have a surface roughness that can promote bone growth and fusion with interbody spacer 10. The surface roughness may be in a range of about 0.10-50 µm, and preferably in a range of about 3-4 µm. As can be appreciated, top and bottom surfaces 22, 24 and opposed side surfaces 26, 28 may include the same or different surface roughness's (i.e., the surface roughness of top surface 22 may be different than the surface roughness of bottom surface 24), or top and bottom surfaces 22, 24 and opposed side surfaces 26, 28 may not include a surface roughness; rather, top and bottom surfaces 22, 24 and opposed side surfaces 26, 28 may be smooth. In embodiments top and bottom surfaces 22, 24 and opposed side surfaces 26, 28 may include any combination of surface roughness or smooth surface. Additionally, body portion 12 includes a plurality of orifices 44 and 46 defined through top and bottom surfaces 22, 24 and opposed side surfaces 26, 28, respectively, configured to promote bone ingrowth. Although illustrated as having a generally circular cross-section, orifices 44 may include any suitable cross-section, as will be described in further detail hereinbelow. Orifices 46 are illustrated as having a generally diamond shaped cross-section, however, it is contemplated that orifices 46 may include any suitable cross-section, as will be described in further detail hereinbelow. The cross-sectional shapes of orifices 44, 46 mimic bone growth along Haversian canals and lamellar structures of bone. The plurality of orifices 44, 46 reduces the density and stiffness of interbody spacer 10 to enable the application of bone putty or the like (e.g., bone-morphogenetic proteins, etc.) to interbody spacer 10 to promote bone ingrowth within interbody spacer 10 and fusion to adjacent vertebral bodies. Bone ingrowth and fusion strengthens interbody spacer 10. In this manner, the likelihood that micromotion would occur would be reduced.

As best illustrated in FIG. 3, the plurality of orifices 44 are arranged in evenly spaced longitudinal rows along longitudinal axis A-A. The plurality of orifices 44 includes orifices with a first diameter 44a, orifices with a second diameter 44b, and orifices with a third diameter 44c. In one non-limiting embodiment, the first diameter 44a is 30 µm, the second diameter 44b is 150 µm, and the third diameter 44c is 500 µm, although other suitable diameters are also contemplated. As can be appreciated, each of the orifices 44 may include a cross-section corresponding to any cross-sectional shape detailed herein. As such, the cross-sectional area of each of orifice 44a, 44b, and 44c may be 0.000707 µm$^2$, 0.0177 µm$^2$, and 0.196 µm$^2$, respectively. In this manner, the plurality of orifices 44 is defined through top and bottoms surfaces 22, 24 and arranged in groups of three orifices, 44a, 44b, 44c, that define a respective pattern along axis A-A of body portion 12.

Figure 4:
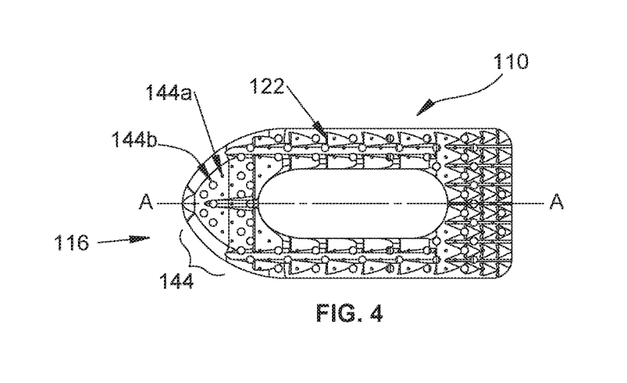
FIG. 4 is a top view of another embodiment of an interbody spacer similar to the interbody spacer of FIG. 1.

Referring to FIG. 4, another embodiment of an interbody spacer provided in accordance with the preset disclosure is illustrated and generally identified by reference numeral 110. Interbody spacer 110 is substantially similar to interbody spacer 10, and therefore only the differences therebetween will be described in detail in the interest of brevity. The orifices of the plurality of orifices 144 include orifices with a first diameter 144a and orifices with a second, larger, diameter 144b. In one non-limiting embodiment, the diameter of the first diameter 144a is 150 µm and the diameter of the second diameter 144b is 500 µm, although other diameters are also contemplated. As can be appreciated, each of the orifices 144 may include a cross-section corresponding to any cross-sectional shape detailed herein. As such, the cross-sectional area of each of orifice 144a and 144b may be 0.0177 µm$^2$ and 0.196 µm$^2$, respectively. In this manner, a pair of rows of orifices 144 having the second, larger diameter 144b is defined through the distal end 116 of top surface 122 and the bottom surfaces (not shown) and extending in a direction transverse to longitudinal axis A-A. A pair of rows of orifices 144 having the first diameter 144a is disposed proximal to the pair of rows of orifices 144 having the second, larger diameter 144b and extends in a direction transverse to longitudinal axis A-A. This pattern is repeated in a proximal (or distal) direction along axis A-A.

Figure 5:
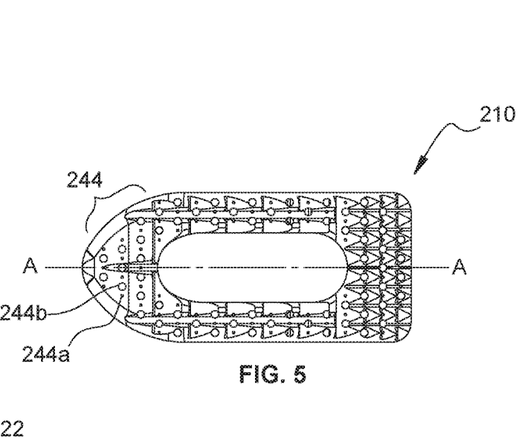
FIG. 5 is a top view of yet another embodiment of an interbody spacer similar to the interbody spacer of FIG. 1.

With reference to FIG. 5, yet another embodiment of an interbody spacer provided in accordance with the present disclosure is illustrated and generally identified by reference numeral 210. Interbody spacer 210 is substantially similar to interbody spacer 10, and therefore only the differences therebetween will be described in detail in the interest of brevity. The plurality of orifices 244 includes orifices having a first diameter 244a and orifices having a second, larger, diameter 244b. In one non-limiting embodiment, the first diameter 244a is 150 µm and the second diameter 244b is 500 µm, although other diameters are also contemplated. As can be appreciated, each of the orifices 244 may include a cross-section corresponding to any cross-sectional shape detailed herein. As such, the cross-sectional area of each of orifice 244a and 244b may be 0.0177 µm$^2$ and 0.196 µm$^2$, respectively. In this manner, the plurality of orifices 244 is defined through top and bottom surfaces 222, 224 such that the diameter of the plurality of orifices 244 alternates between orifices having the first diameter 244a and orifices having the second, larger, diameter 244b in a direction along longitudinal axis A-A. This pattern is offset in a direction transverse to longitudinal axis A-A such that an orifice of the plurality of orifices 244 having a first diameter 244a is only adjacent an orifice of the plurality of orifices 244 having a second, larger, diameter 244b.

Figure 6:
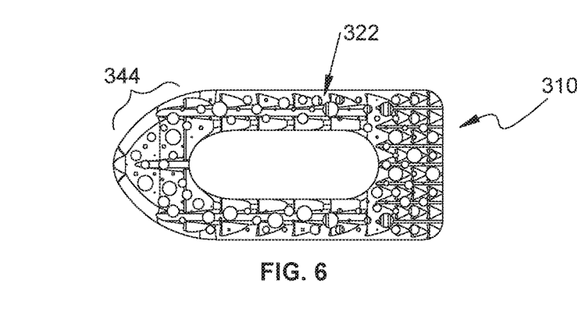
FIG. 6 is a top view of still another embodiment of an interbody spacer similar to the interbody spacer of FIG. 1.

With reference to FIG. 6, still another embodiment of an interbody spacer provided in accordance with the present disclosure is illustrated and generally identified by reference numeral 310. Interbody spacer 310 is substantially similar to interbody spacer 10, and therefore only the differences therebetween will be described in detail in the interest of brevity. The plurality of orifices 344 includes orifices of various diameters. In one non-limiting embodiment, the diameter of each orifice of the plurality of orifices 344 may vary between 50 µm and 1000 µm. As can be appreciated, each of the orifices 344 may include a cross-section corresponding to any cross-sectional shape detailed herein. As such, the cross-sectional area of each of orifice 344 may be 0.0707 µm$^2$ and 0.385 µm$^2$. The plurality of orifices 344 is defined through top surface 322 and the bottom surfaces (not shown) in a random manner such that there are no defined rows, and the diameters of each orifice of the plurality of orifices 344 vary.

Figure 7:
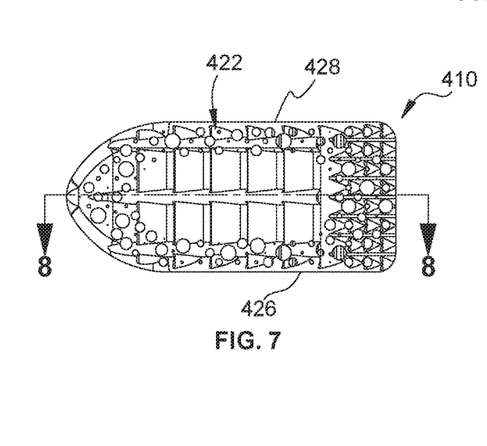
FIG. 7 is a top view of another embodiment of an interbody spacer similar to the interbody spacer of FIG. 1, without a cavity extending therethrough.
Figure 8:
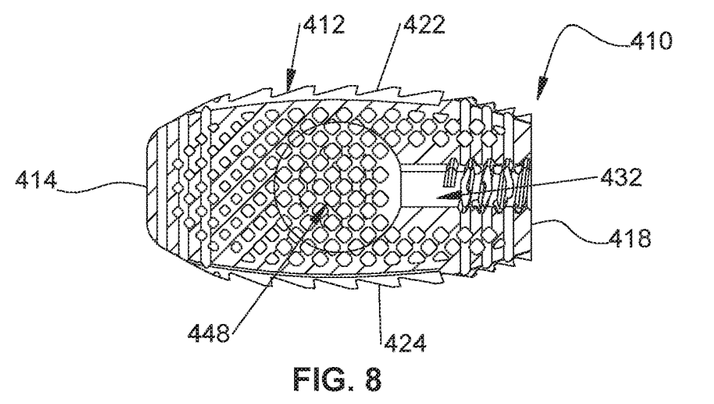
FIG. 8 is a side, cross-sectional, view of the interbody spacer of FIG. 7, taken along section-line 8-8 of FIG. 7.
Figure 8A:
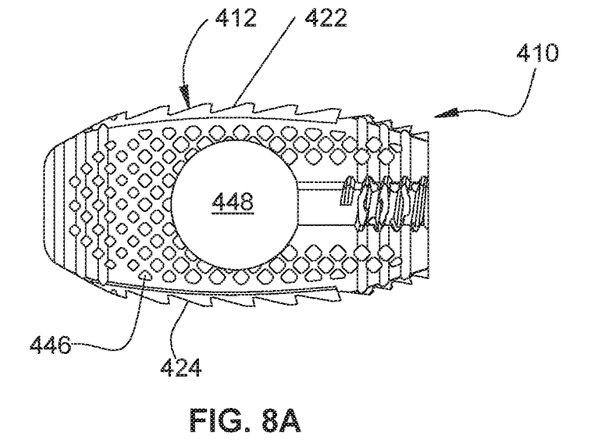
FIG. 8A is a side, cross-sectional, view of an alternate embodiment of the interbody spacer of FIG. 7, taken along section-line 8-8 of FIG. 7.

Referring now to FIGS. 7 and 8, an alternate embodiment of an interbody spacer provided in accordance with the present disclosure is illustrated and generally identified by reference numeral 410. Interbody spacer 410 is substantially similar to interbody spacer 10, and therefore, only the differences therebetween will be described in detail in the interest of brevity. Interbody spacer 410 does not include a through-bore defined through top surface 422 and the bottom surfaces (not shown). Rather, as best illustrated in FIG. 8, interbody spacer 410 includes a void 448 defined within an interior portion of body 412. In this manner, void 448 does not breach leading or trailing surface 414, 418, top or bottom surface 422, 424, or the opposed side surfaces 426, 428 (FIG. 7). In one non-limiting embodiment, aperture 432 extends through a proximal end of void 448 such that aperture 432 is in open communication therewith. Although illustrated as having a generally circular cross-section, it is contemplated that void 448 may include any suitable shape and/or volume, such as spheroid, ovoid, cuboid, rectanguloid, ellipsoid, or the like. In certain embodiments, void 448 may include an amorphous shape. Additionally, as best illustrated in FIG. 8A, it is contemplated that void 448 may be isolated from the plurality of orifices defined through top surface 422 and the plurality of orifices 446 defined through the opposed side surfaces 426, 428 (FIG. 7), or only one or the other. It is further contemplated that void 448 may include one or more protrusions (not shown) extending towards an interior portion of void 448. As can be appreciated, the one or more protrusions may include any suitable shape, such as frusto conical, spheroid, ovoid, cuboid, rectanguloid, conical, ellipsoid, or the like. By varying the shape and or volume of void 448, the density and stiffness of interbody spacer 410 may be likewise varied, thereby allowing a clinician to select an implant more closely tailored to the density of adjacent vertebral bodies. In embodiments, interbody spacer 448 may include a plurality of smaller voids 448 defined in an interior portion of body 412.

Figure 8B:
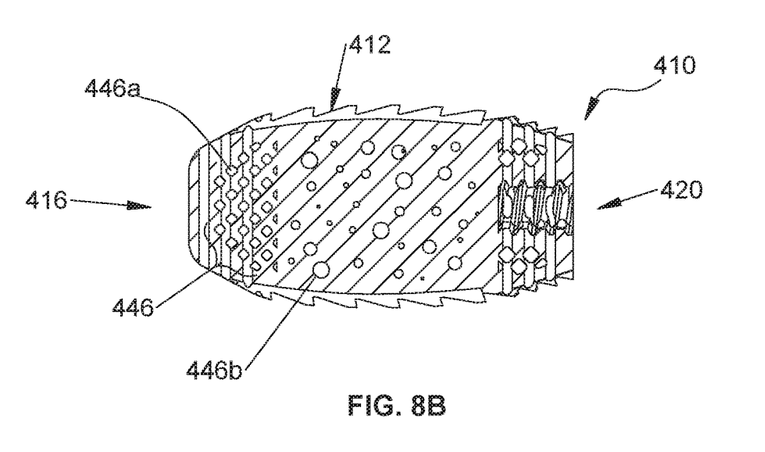
FIG. 8B is a side, cross-sectional, view of an alternate embodiment of the interbody spacer of FIG. 8, taken along section-line 8-8 of FIG. 7.

Alternatively, as best illustrated in FIG. 8B, interbody spacer 410 may include no through-bore or void. In this manner, aperture 432 is blind (i.e., terminates in a distal face in an interior portion of interbody spacer 410). Additionally, the plurality of orifices 446 defined through the opposed side surfaces includes a diamond shaped cross-section 446a on distal and proximal ends 416, 420 and a random array of orifices having a circular cross-section 446b and varying diameters defined through the opposed side surfaces (not shown) at a medial portion of body 412. As can be appreciated, the plurality of orifices 446 having a diamond-shaped cross-section 446a may be defined through the medial portion of the opposed side surfaces and the random array of circular orifices 446b may be defined through distal and proximal ends 416, 420 of the opposed side surfaces, or any combination thereof.

Figure 9:
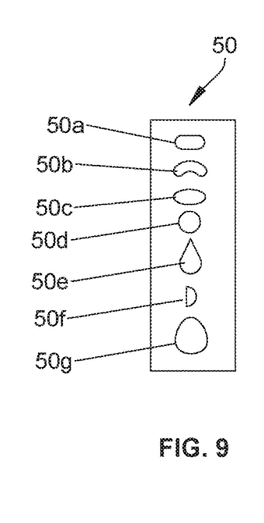
FIG. 9 is an illustration of a family of cross-sectional shapes for an orifice defined through an interbody spacer in accordance with the present disclosure.

Referring now to FIGS. 9-15, the plurality of orifices 44, 46 may include various cross-sectional shapes of differing families. As illustrated in FIG. 9, orifices 44, 46 may include a cross-sectional shape having varying curvature, designated as a first family 50. Cross-sectional shapes included in first family 50 include oval 50a, kidney 50b, elliptical 50c, circular 50d, teardrop 50e, semicircle 50f, and ovoid 50g. As can be appreciated, orifices 44, 46 from first family 50 may include any cross-sectional shape having an arcuate, curvate, or otherwise amorphous shape not otherwise illustrated in FIG. 9.

Figure 10:
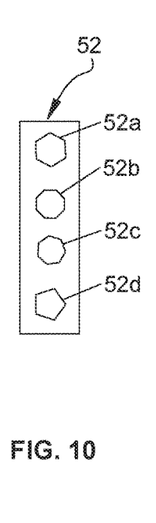
FIG. 10 is an illustration of another family of cross-sectional shapes for an orifice defined through an interbody spacer in accordance with the present disclosure.

A second family 52 of cross-sectional shapes having more than four sides is illustrated in FIG. 10. In this manner, the plurality of orifices 44, 46 may include a cross-sectional shape of a hexagon 52a, an octagon 52b, a heptagon 52c, and a pentagon 52d. As can be appreciated, any polygon having more than four sides may be included in second family 52, such as nonagon, decagon, dodecagon, etc.

Figures 11, 12, 13:
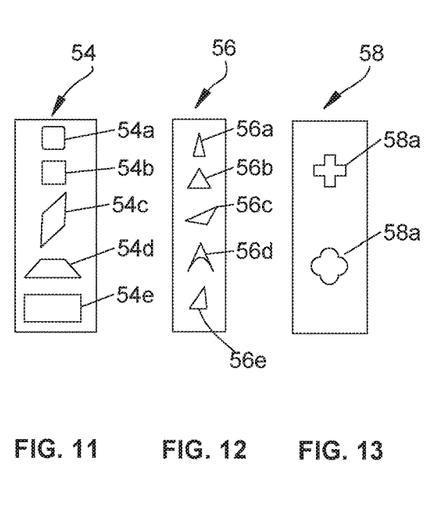
FIG. 11 is an illustration of yet another family of cross-sectional shapes for an orifice defined through an interbody spacer in accordance with the present disclosure.
FIG. 12 is an illustration of still another family of cross-sectional shapes for an orifice defined through an interbody spacer in accordance with the present disclosure.
FIG. 13 is an illustration of another family of cross-sectional shapes for an orifice defined through an interbody spacer in accordance with the present disclosure.

With reference to FIG. 11, a third family 54 of cross-sectional shapes from which the plurality of orifices 44, 46 may be defined is illustrated. Third family 54 includes quadrilaterals, such as a square with rounded edges 54a (such as a squircle), square 54b, rhombus 54c, trapezoid 54d, and rectangle 54e. As can be appreciated, third family 54 may include any quadrilateral, such as parallelogram, kite, isosceles trapezoid, trapezium, etc.

A fourth family 56 of cross-sectional shapes from which the plurality of orifices 44, 46 may be defined is illustrated in FIG. 12. Fourth family 56 includes triangles, such as isosceles 56a, equilateral 56b, scalene 56c, arrowhead with arcuate base 56d, and right 56e. As can be appreciated, fourth family 56 may include any type of triangle known in the art.

FIG. 13 illustrates a fifth family 58 of cross-sectional shapes from which the plurality of orifices 44, 46 may be defined. Fifth family 58 includes a greek cross 58a and clover 58b, although other similar cross-sectional shapes are contemplated, like, cross, star, or the like.

Figures 14, 15:
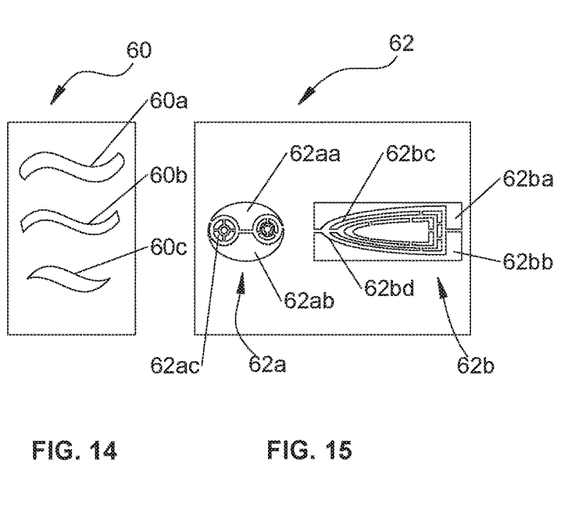
FIG. 14 is an illustration still another family of cross-sectional shapes for an orifice defined through an interbody spacer in accordance with the present disclosure.
FIG. 15 is an illustration of yet another family of cross-sectional shapes for an orifice defined through an interbody spacer in accordance with the present disclosure.

As illustrated in FIG. 14, a sixth family 60 of cross-sectional shapes from which the plurality of orifices 44, 46 may be defined includes sinusoidal shapes having various lengths, widths, and number of sides. A first sinusoidal shape 60a includes a width that is larger than that of a second sinusoidal shape 60b. A third sinusoidal shape 60c includes pointed opposed ends. As can be appreciated, any suitable sinusoidal shape may be included in sixth family 60.

FIG. 15 illustrates a seventh family 62 of cross-sectional shapes from which the plurality of orifices 44, 46 may be defined. The cross-sectional shapes included in the seventh family 62 include ornate designs having various circular designs as illustrated in first design 62a or rectangular designs as illustrated in second design 62b. First design 62a includes upper and lower apertures 62aa and 62ab defining a generally oval shape. First design 62a includes a plurality of additional bores 62ac defined in an interior portion thereof. In this manner, a plurality of circular features resembling wheels and spokes and/or pinwheels are defined. The plurality of bores 62ac define a corresponding plurality of bridges or spokes 62ad that separate each of each of the upper and lower apertures 62aa, 62ab, and plurality of bores 62ac.

Similarly, second design 62b includes upper and lower apertures 62ba and 62bb defining a generally rectangular shape. A plurality of elongate, arcuate, bores 62bc are defined in an interior portion of second design 62b, the plurality of elongate, arcuate, bores 62bc defining cooperating to define a generally triangular shape. The plurality of elongate, arcuate, bores 62bc define a corresponding plurality of bridges 62bd that separate each of the upper and lower apertures 62ba, 62bb and plurality of bores 62bc.

As can be appreciated, any of the above described families may be interchanged or randomly selected as the cross-sectional shape of orifices 44, 46 defined through upper and lower surfaces 22, 24 or opposed side surfaces 26, 28, respectively, of body portion 12. In embodiments, the plurality of orifices 44 defined through top surface 22 may utilize a different cross-sectional shape than that of the plurality of orifices 44 defined through bottom surface 24. Similarly, the plurality of orifices 46 defined through side surface 26 may include a different cross-sectional shape than the plurality of orifices 46 defined through opposite side surface 28. It is contemplated that any number of combinations of cross-sectional shapes may be employed.

Figures 16, 17:
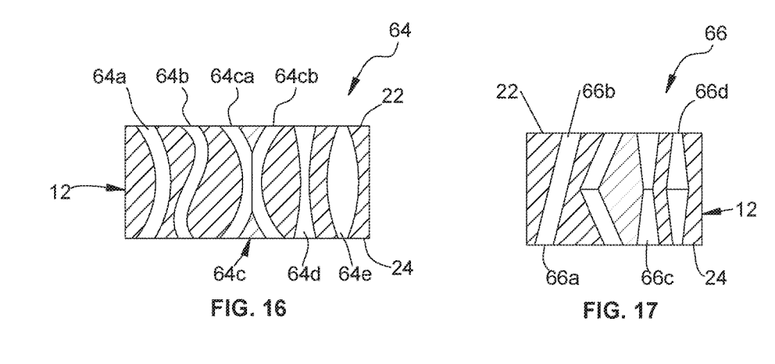
FIG. 16 is a side, cross-sectional view, of a family shapes for a channel defined through an interbody spacer in accordance with the present disclosure.
FIG. 17 is a side, cross-sectional view, of another family of shapes for a channel defined through an interbody spacer in accordance with the present disclosure.

Referring now to FIGS. 16-23, the plurality of orifices 44, 46 defined through top and bottom surfaces 22, 24 and opposed side surfaces 26, 28 define a respective channel through body portion 12. FIGS. 16-23 illustrate a variety of families of channels that may be defined through body portion 12. As best illustrated in FIG. 16, a first family of channels 64 having a generally arcuate profile is illustrated. The first family of channels 64 includes a first channel 64a having a generally arcuate profile. First channel 64a includes a pair of bowed or bulging sidewalls and includes a constant width. A second channel 64b includes a generally sinusoidal profile. A third channel 64c includes a pair of channels 64ca, 64cb defining a generally X-shaped configuration. In this manner, channel 64ca of the pair of channels is bowed in a first direction and channel 64cb of the pair of channels bows in an opposite direction, such that channels 64ca, 64cb intersect (i.e., channels 64ca and 64cb are in open communication). A fourth channel 64d includes a generally hourglass profile. A fifth channel 64e includes an elliptical profile. As can be appreciated, first family of channels 64 may include any suitable profile having arcuate sidewalls.

FIG. 17 illustrates a second family of channels 66 having generally planar sidewalls. First channel 66a includes planar sidewalls extending in a diagonal direction such that the openings of an orifice of the plurality of orifices 44, 46 on the top and bottom surfaces 22, 24, respectively, are offset in relation to one another. A second channel 66b includes a generally arrowhead or rotated chevron type profile (i.e., upper and lower portions extending diagonally toward one another in a medial portion of body portion 12 to define a point). A third channel 66c includes a generally hourglass profile having planar sidewalls. A fourth channel 66d includes a generally inverted hourglass profile (i.e., the width of fourth channel 66d increases at a middle portion thereof).

Figure 18:
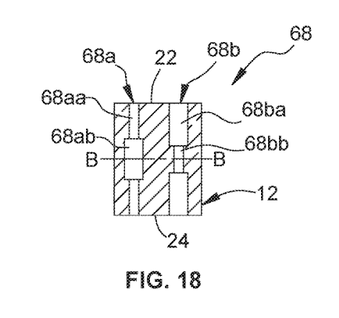
FIG. 18 is a side, cross-sectional view, of yet another family of shapes for a channel defined through an interbody spacer in accordance with the present disclosure.

A third family of channels 68 is illustrated in FIG. 18. Each channel of the third family of channels 68 is mirrored about axis B-B defined at a medial portion of body 12. A first channel 68a is defined through top surface 22 and includes a first cylinder 68aa having a first diameter extending towards bottom surface 24. First cylinder 68aa transitions to a second cylinder 68ab and includes a second, larger, diameter than the diameter of first cylinder 68aa. A second channel 68b is essentially an inverse of first channel 68a. In particular, a first cylinder 68ba having a first diameter intersects top surface 22 and extends towards bottom surface 24. First cylinder 68ba transitions to a second cylinder 68bb and includes a second, smaller, diameter than the diameter of first cylinder 68ba.

Figure 19:
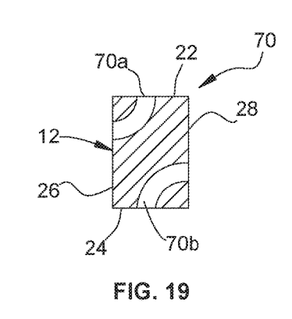
FIG. 19 is a side, cross-sectional view, of still another family of shapes for a channel defined through an interbody spacer in accordance with the present disclosure.

Referring now to FIG. 19, a fourth family of channels 70 is illustrated. A first channel 70a is defined through top surface 22 of body portion 12 and includes a generally arcuate shape such that first channel 70a curves towards, and extends through, one of opposed side surfaces 26, 28. A second channel 70b is defined through bottom surface 24 of body portion 12 and includes a generally arcuate shape such that second channel 70b curves towards, and extends through, an opposite one of opposed side surfaces 26, 28 than that of first channel 70a.

Figure 20:
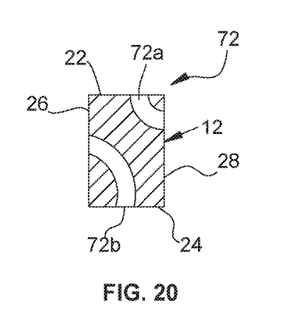
FIG. 20 is a side, cross-sectional view, of another family of shapes for a channel defined through an interbody spacer in accordance with the present disclosure.

FIG. 20 illustrates a fifth family of channels 72 including similar profile to that of the fourth family of channels 70. In this manner, a first channel 72a includes a tighter radius of curvature than that of a second, opposed channel 72b. As can be appreciated, second channel 72b may have a tighter radius than that of first channel 72a.

Figure 21:
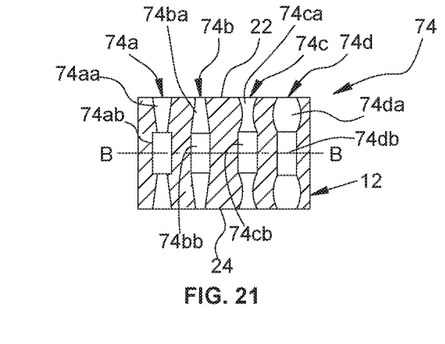
FIG. 21 is a side, cross-sectional view, of still another family of shapes for a channel defined through an interbody spacer in accordance with the present disclosure.

A sixth family of channels is illustrated in FIG. 21 and is generally identified by reference numeral 74. Each channel of the third family of channels 74 is mirrored about axis B-B defined at a medial portion of body 12. A first channel 74a includes a frusto conical profile 74aa defined through top surface 22 of body portion 12 extending towards bottom surface 24. Frusto conical profile 74aa includes a generally inverted orientation (i.e., the diameter decreases in a direction from top surface 22 towards bottom surface 24). Frusto conical profile 74aa transitions to a cylindrical profile 74ab at a medial portion of body portion 12 having a larger diameter than that of the portion of frusto conical profile 74aa that intersect cylindrical profile 74ab.

A second channel 74b includes a substantially similar profile to that of first channel 74a except that the frusto conical profile 74ba is inverted with respect to frusto conical profiles 74aa of first channel 74a.

Third channel 74c includes first portion 74ca having a generally hourglass configuration that intersects top surface 22 of body portion 12 and extends towards bottom surface 24. First portion 74ca transitions to a second portion 74cb having a generally cylindrical configuration at a medial portion of body portion 12.

A fourth channel 74d includes a first portion 74da having a generally spherical configuration. First portion 74da is defined through top surface 22 of body portion 12 and extends towards bottom surface 24. First portion 74da transitions to a second portion 74db having a generally cylindrical configuration at a medial portion of body portion 12. Second portion 74db includes a diameter less than the diameter of first portion 74da.

Figure 22:
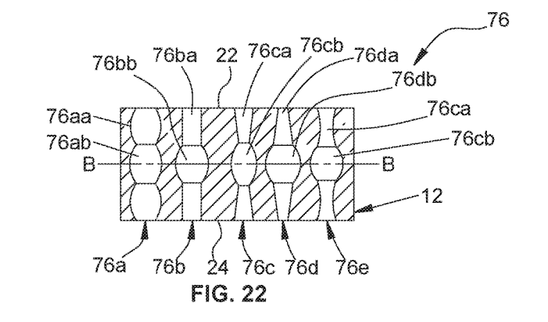
FIG. 22 is a side, cross-sectional view, of yet another family of shapes for a channel defined through an interbody spacer in accordance with the present disclosure.

FIG. 22 illustrates a seventh family of channels generally identified by reference numeral 76. Each channel of the third family of channels 76 is mirrored about axis B-B defined at a medial portion of body 12. A first channel 76a includes a first and second spherical portion 76aa and 76ab respectively, disposed in a generally stacked configuration such that first spherical portion extends through upper surface 22 of body 12. Each of first and second spherical portions 76ca and 76cb include a generally similar diameter, although other configurations are also contemplated.

A second channel 76b includes a first portion 76ba defined through top surface 22 of body portion 12 and extending towards bottom surface 24. First portion 76ba includes a generally cylindrical configuration and transitions to a second portion 76bb having a generally spherical configuration at a medial portion of body portion 12.

Third channel 76c includes a first portion 76ca having a generally inverted frusto conical configuration (i.e., the diameter of first portion decreases in a direction from top surface 22 towards bottom surface 24). First portion 76ca is defined through top surface 22 of body portion 12 and extends towards bottom surface 24. First portion 76ca transitions to a second portion 76cb having a generally ellipsoid configuration at a medial portion of body portion 12, although it is contemplated that second portion 76cb may include a generally spherical configuration similar to that of second portion 76bb of second channel 76b.

Fourth channel 76d is similar to that of third channel 76c except that the first portions 76da includes a frusto conical configuration that is inverted relative to first portion 76ca of third channel 76c. Second portion 76db includes a generally spherical configuration.

A fifth channel 76e includes a first portion 76ea having a generally hourglass configuration. First portion 76ea is defined through top surface 22 of body portion 12 and extends towards bottom surface 24. First portion 76ea transitions to a second portion 76eb having a generally spherical configuration at a medial portion of body portion 12.

Figure 23:
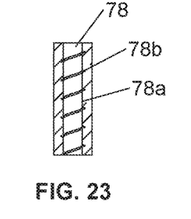
FIG. 23 is a side, cross-sectional view, of still another family of shapes for a channel defined through an interbody spacer in accordance with the present disclosure.

FIG. 23 illustrates an eighth channel 78 defined through top and bottom surfaces 22, 24 of body portion 12. Eighth channel 78 includes a generally cylindrical profile including helical grooves 78b defined on an inner sidewall 78a thereof.

Although each orifice and channel has been hereinabove described as being defined through top and bottom surfaces 22, 24 of body 12, as can be appreciated, the orifices and channels may be defined through opposed side surfaces 26, 28.

As can be appreciated, manufacturing interbody spacers 10, 110, 210, 310, and 410 using standard machining methods (e.g., lathe, mill, EDM, etc.) could be difficult. In view of this, it is contemplated that in addition to manufacturing interbody spacers 10, 110, 210, 310, and 410 using the aforementioned conventional means, interbody spacers 10, 110, 210, 310, and 410 may be manufactured by means of additive manufacturing methods (e.g., SDM, SLPP, DMLS (i.e., EOS), SLS, SLM, SHS, EBM, VAT photopolymerisation, material jetting, binder jetting, or the like). In one non-limiting embodiment, interbody spacers 10, 110, 210, 310, and 410 may be manufactured using Selective Laser Powder Processing (SLPP). SLPP utilizes powdered metal and a laser which sinters or cures the metal in a selective fashion according to the design intent in thin layers. In embodiments, the layers have a thickness of about 250 µm. Interbody spacers 10, 110, 210, 310, and 410 are built layer by layer to allow for more design options and features that would be difficult to be machined using conventional methods. Specifically, a first layer of powder is applied to a specialized build plate, at which point the laser cures portions of the powder according to the design intent. At this point, a second layer is applied to the build plate and the laser is again used to cure selective portions of this second layer. This process is repeated until interbody spacers 10, 110, 210, 310, and 410 are fully formed. Once interbody spacers 10, 110, 210, 310, and 410 are fully formed, uncured powder is removed using compressed air or other similar means. Next, post machining is performed on interbody spacers 10, 110, 210, 310, and 410 to remove any burrs or similar imperfections embedded within interbody spacers 10, 110, 210, 310, and 410 during the additive manufacturing process. In embodiments, the burrs are removed by means of buffer wheels, clippers, files, or the like. Once de-burred, interbody spacers 10, 110, 210, 310, and 410 are heat treated, and thereafter, media blasted using aluminum oxide. Thereafter, interbody spacers 10, 110, 210, 310, and 410 are immersed in a hydrofluoric bath to strip the aluminum oxide therefrom. Finally, interbody spacers 10, 110, 210, 310, and 410 are inspected by quality control personnel (or using automated means), cleaned via ultrasonic cleaning, dried, and packaged. It is contemplated that the design of interbody spacers 10, 110, 210, 310, and 410 may be customized for each specific patient using SLPP. For a detailed description of exemplary manufacturing methods, reference may be made to U.S. Pat. No. 8,590,157, issued on Nov. 26, 2013 to Kruth et al., the entire contents of which are hereby incorporated by reference herein.

Interbody spacers 10, 110, 210, 310, and 410 may be constructed from commercially pure titanium, titanium alloy, cobalt-chrome, ceramic, Polyetheretherketone (PEEK), or any other suitable biocompatible material. In embodiments, interbody spacers 10, 110, 210, 310, and 410 may be manufactured using a three-dimensional printer utilizing a biocompatible polymer.

With reference to FIGS. 1-8B, in use, an intervertebral space is first prepared, e.g., damaged or diseased tissue is removed. As the construction of interbody spacer 10 is similar to that of interbody spacers 110, 210, 310, and 410, only the method of use of interbody spacer 10 will be described in detail for purposes of brevity. An appropriately sized interbody spacer 10 is selected based on the patient's spinal characteristics and the desired amount of lordosis. Next, the interior space of through-bore 34 of body portion 12 may be packed with bone in-growth material, drugs, or other suitable materials or compounds. Examples of such materials are allograft material, or synthetic materials comprised of a biocompatible, osteoconductive, osteoinductive, or osteogeneic material such as VITOSS® Synthetic Cancellous Bone Void Filler material. Next, a suitable insertion instrument (not shown) is threaded into aperture 32 of body portion 12 until interbody spacer 10 is securely affixed to the insertion instrument. At this point, interbody spacer 10 is advanced within an incision within the patient, and thereafter, the previously prepared inverterterbal space of the patient's spine. Once interbody spacer 10 is placed within the intervertebral space such that interbody spacer 10 rests on the distal apophyseal ring of the vertebral body, the tool (not shown) is released from aperture 32, and thereafter, the incision within the patient. By residing on the apophyseal ring, interbody spacer 10 is less likely to experience subsidence into the end plates which will facilitate fusion between the intervertebral plates.

This process may be repeated as many times as the procedure requires, whether it be for the same interbody spacer 10 or for a plurality of interbody spacers 10 as required by the procedure being performed.

It is envisioned that the manufacturing processes and orifice designs detailed above may be utilized to form various other medical devices known in the art. In this manner, the additive manufacturing process detailed above may be employed to form corpectomy devices, fixed spinal implants, expandable spinal implants, bone screws, cervical implants, and the like. Similarly, the orifice designs detailed above may be formed in any of the beforementioned medical devices that would benefit from an increased ability to fuse with bone. Examples of such devices may be found in the following commonly owned references: U.S. Pat. No. 8,585,761 to Theofilos, U.S. Pat. No. 8,673,011 to Theofilos et al., U.S. application Ser. No. 14/936,911 to Sutterlin et al., U.S. Pat. No. 8,801,791 to Soo et al., U.S. Pat. No. 8,439,977 to Kostuik et al., U.S. Patent Application Publication No. 2010/0100131 to Wallenstein, U.S. Patent Application Publication No. 2012/0179261 to Soo, U.S. Pat. No. 8,449,585 to Wallenstein et al., U.S. Pat. No. 8,814,919 to Barrus et al., U.S. Pat. No. 5,733,286 to Errico et al., and U.S. Patent Application Publication No. 2013/0046345 to Jones et al.

It will be understood that various modifications may be made to the embodiments of the presently disclosed interbody spacer. Therefore, the above description should not be construed as limiting, but merely as exemplifications of embodiments. Those skilled in the art will envision other modifications within the scope and spirit of the present disclosure.

The invention claimed is:
1. An interbody spacer, comprising:
a homogenous body portion including a distal end portion, a proximal end portion, opposed side surfaces that extend between the distal and proximal end portions, and top and bottom surfaces configured and adapted to engage vertebral bodies;
first orifices defined through the top surface;
second orifices defined through the bottom surface, a respective orifice of the first and second orifices is in open communication thereby defining an uninterrupted channel therebetween, and
an internal void disposed within the homogenous body portion, wherein a cross-section of the void is substantially larger than cross-sections of any of the first and second orifices.

2. The interbody spacer of claim 1, wherein the internal void is in communication with the one or more channels.

3. The interbody spacer of claim 1, wherein the internal void is separated from the one or more channels such that the internal void is not in communication with the one or more channels.

4. The interbody spacer of claim 1, wherein the internal void does not breach any of the distal end portion, proximal end portion, opposed side surfaces, and top and bottom surfaces of the homogenous body portion such that the internal void is completely encapsulated within the homogenous body portion.

5. The interbody spacer of claim 4, wherein the internal void defines a spheroidal cavity.

6. An interbody spacer, comprising:
a homogenous body portion including a distal end portion, a proximal end portion, opposed side surfaces that extend between the distal and proximal end portions, and top and bottom surfaces configured and adapted to engage vertebral bodies;
first orifices defined through the top surface; and
second orifices defined through the bottom surface, wherein a respective orifice of the first and second orifices is in open communication thereby defining an uninterrupted channel therebetween,
wherein the channel includes grooves extending from the top surface to the bottom surface.

7. The interbody spacer of claim 6, wherein the grooves are helical grooves.

8. The interbody spacer of claim 6, wherein the body portion is formed from powder processed using Selective Laser Powder Processing.

9. An interbody spacer, comprising:
a homogenous body portion including a distal end portion, a proximal end portion, first and second opposed side surfaces that extend between the distal and proximal end portions, and top and bottom surfaces configured and adapted to engage vertebral bodies;
first orifices defined through the top surface;
second orifices defined through the first side surface;
third orifices defined through the second side surface, and
fourth orifices defined through the bottom surface, wherein a respective orifice of the first and second orifices is in open communication thereby defining an uninterrupted first channel therebetween, and a respective orifice of the third and fourth orifice is in open communication thereby defining an uninterrupted second channel therebetween.

10. The interbody spacer of claim 9, wherein a first distance traversed by the first channel is different from a second distance traversed by the second channel.

11. The interbody spacer of claim 10, wherein the first distance is greater than the second distance.

12. The interbody spacer of claim 9, wherein the body portion is formed from powder processed using Selective Laser Powder Processing.

13. The interbody spacer of claim 9, wherein each of the first and second channels include grooves extending from the top surface to the bottom surface.

14. The interbody spacer of claim 13, wherein the grooves are helical grooves.

* * * * *